(12) United States Patent
Ressemann et al.

(10) Patent No.: US 8,353,850 B2
(45) Date of Patent: Jan. 15, 2013

(54) STEERABLE GUIDE WIRE WITH TORSIONALLY STABLE TIP

(75) Inventors: Thomas V Ressemann, St. Cloud, MN (US); Peter T Keith, St. Paul, MN (US); Steven N Willard, Bloomington, MN (US); Peter J Ness, Minneapolis, MN (US); Steven S. Hackett, Maple Grove, MN (US)

(73) Assignee: St. Jude Medical, Cardiology Division, Inc., Maple Grove, MN (US)

( * ) Notice: Subject to any disclaimer, the term of this patent is extended or adjusted under 35 U.S.C. 154(b) by 389 days.

(21) Appl. No.: 12/484,910

(22) Filed: Jun. 15, 2009

(65) Prior Publication Data

US 2009/0318835 A1 Dec. 24, 2009

Related U.S. Application Data

(63) Continuation of application No. 11/652,234, filed on Jan. 10, 2007, now abandoned, which is a continuation-in-part of application No. 11/176,485, filed on Jul. 7, 2005, now Pat. No. 8,267,872.

(51) Int. Cl.
*A61B 5/00* (2006.01)
(52) U.S. Cl. ..................................... 600/585
(58) Field of Classification Search .................. 600/585
See application file for complete search history.

(56) References Cited

U.S. PATENT DOCUMENTS

| | | | |
|---|---|---|---|
| 3,612,058 A | 10/1971 | Ackerman | |
| 4,579,127 A | 4/1986 | Haacke | |
| 4,682,607 A | 7/1987 | Vaillancourt et al. | |
| 4,763,647 A * | 8/1988 | Gambale | 600/434 |
| 4,867,173 A | 9/1989 | Leoni | |
| 4,932,419 A | 6/1990 | De Toledo | |
| 4,967,753 A | 11/1990 | Haase et al. | |
| 5,007,434 A | 4/1991 | Doyle et al. | |
| 5,063,935 A | 11/1991 | Gambale | |
| 5,144,959 A * | 9/1992 | Gambale et al. | 600/585 |
| 5,203,772 A | 4/1993 | Hammerslag et al. | |
| 5,228,453 A | 7/1993 | Sepetka | |
| 5,299,580 A | 4/1994 | Atkinson et al. | |
| 5,377,690 A | 1/1995 | Berthiaume | |
| 5,379,779 A | 1/1995 | Rowland et al. | |
| 5,542,434 A | 8/1996 | Imran et al. | |
| 5,769,796 A * | 6/1998 | Palermo et al. | 600/585 |
| 5,772,609 A * | 6/1998 | Nguyen et al. | 600/585 |
| 5,827,201 A | 10/1998 | Samson et al. | |
| 5,833,631 A * | 11/1998 | Nguyen | 600/585 |
| 5,902,254 A | 5/1999 | Magram | |
| 5,938,623 A | 8/1999 | Quiachon et al. | |

(Continued)

FOREIGN PATENT DOCUMENTS

WO 2005/016433 2/2005

(Continued)

*Primary Examiner* — Jeffrey G Hoekstra
(74) *Attorney, Agent, or Firm* — Holland & Hart LLP

(57) ABSTRACT

A steerable guide wire includes a core wire having a proximal end and a distal end. A braided filament is affixed to the distal end of the core wire. An outer coil surrounds at least a portion of the core wire and the braided filament. A proximal end of the braided filament is secured to a distal end of the coil. By locating the braided filament in the distal tip portion of the guide wire, a guide wire is provided that is highly flexible, has a high degree of tensile integrity, and is highly steerable, even in tortuous vasculature. Filter and balloon catheters having braided filaments at the distal end are also described.

28 Claims, 10 Drawing Sheets

U.S. PATENT DOCUMENTS

| | | |
|---|---|---|
| 5,951,496 A | 9/1999 | Willi |
| 6,017,319 A | 1/2000 | Jacobsen et al. |
| 6,019,736 A * | 2/2000 | Avellanet et al. ............. 600/585 |
| 6,139,510 A * | 10/2000 | Palermo ........................ 600/585 |
| 6,159,165 A * | 12/2000 | Ferrera et al. ................. 600/585 |
| 6,168,570 B1 | 1/2001 | Ferrera |
| 6,183,420 B1 * | 2/2001 | Douk et al. ................... 600/462 |
| 6,190,353 B1 | 2/2001 | Makower et al. |
| 6,344,029 B1 | 2/2002 | Estrada et al. |
| 6,383,146 B1 | 5/2002 | Klint |
| 6,428,489 B1 | 8/2002 | Jacobsen et al. |
| 6,440,088 B1 | 8/2002 | Jacobsen et al. |
| 6,488,637 B1 | 12/2002 | Eder et al. |
| 6,579,246 B2 | 6/2003 | Jacobsen et al. |
| 6,579,278 B1 * | 6/2003 | Bencini ........................ 604/528 |
| 6,669,652 B2 | 12/2003 | Anderson et al. |
| 6,679,853 B1 * | 1/2004 | Jalisi ............................ 600/585 |
| 6,706,055 B2 | 3/2004 | Douk et al. |
| 6,955,657 B1 | 10/2005 | Webler |
| 7,618,379 B2 * | 11/2009 | Reynolds et al. ............. 600/585 |
| 2003/0069521 A1 * | 4/2003 | Reynolds et al. ............. 600/585 |
| 2003/0181827 A1 | 9/2003 | Hojeibane et al. |
| 2003/0181828 A1 | 9/2003 | Fujimoto et al. |
| 2004/0039304 A1 | 2/2004 | Connors et al. |
| 2004/0054301 A1 | 3/2004 | Cassell et al. |
| 2004/0102719 A1 | 5/2004 | Keith et al. |
| 2004/0111044 A1 | 6/2004 | Davis et al. |
| 2004/0143265 A1 | 7/2004 | Landry et al. |
| 2004/0193073 A1 * | 9/2004 | DeMello et al. .............. 600/585 |
| 2004/0260206 A1 | 12/2004 | Murayama et al. |
| 2005/0027212 A1 | 2/2005 | Segner et al. |
| 2005/0038359 A1 | 2/2005 | Aimi et al. |
| 2005/0080356 A1 | 4/2005 | Dapolito et al. |
| 2006/0064036 A1 * | 3/2006 | Osborne et al. ............... 600/585 |

FOREIGN PATENT DOCUMENTS

| | | |
|---|---|---|
| WO | 2005/027212 | 3/2005 |
| WO | 2005/092422 | 10/2005 |

* cited by examiner

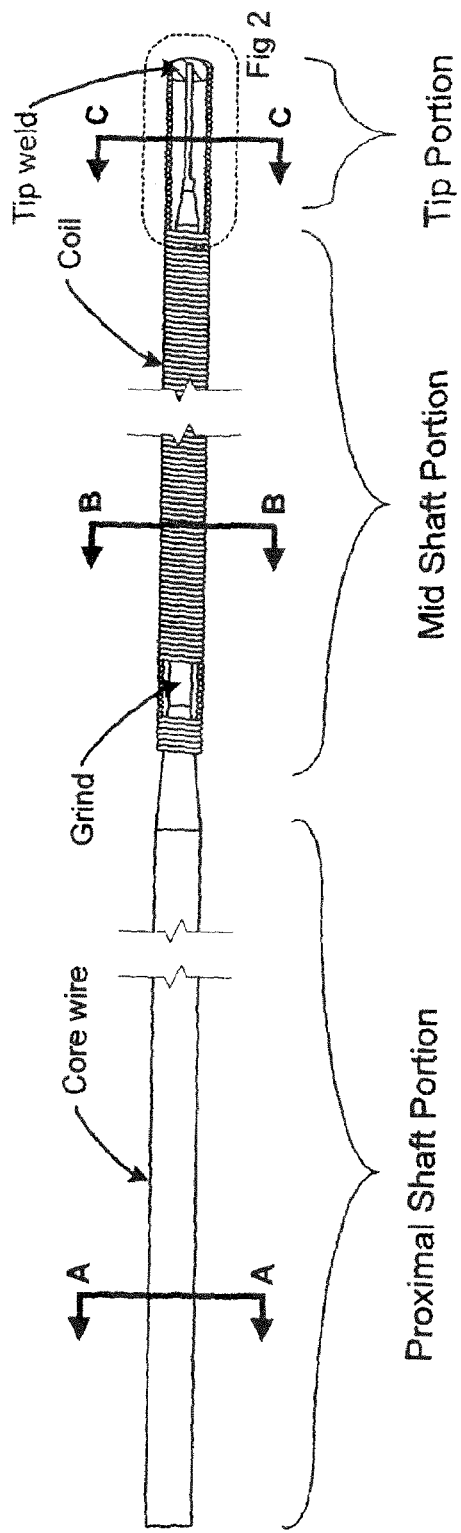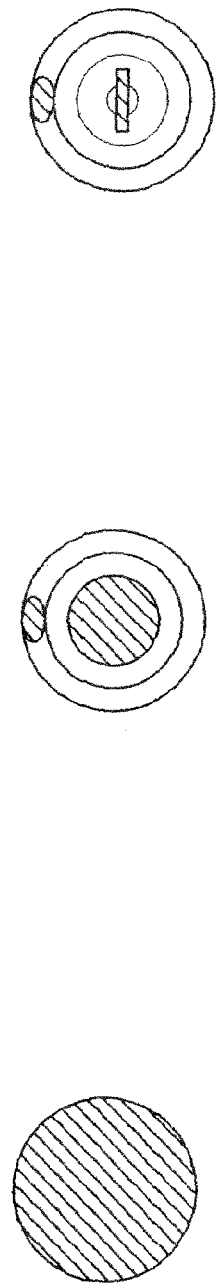
FIG. 1A (Prior Art)
FIG. 1B (Prior Art) Section A-A
FIG. 1C (Prior Art) Section B-B
FIG. 1D (Prior Art) Section C-C

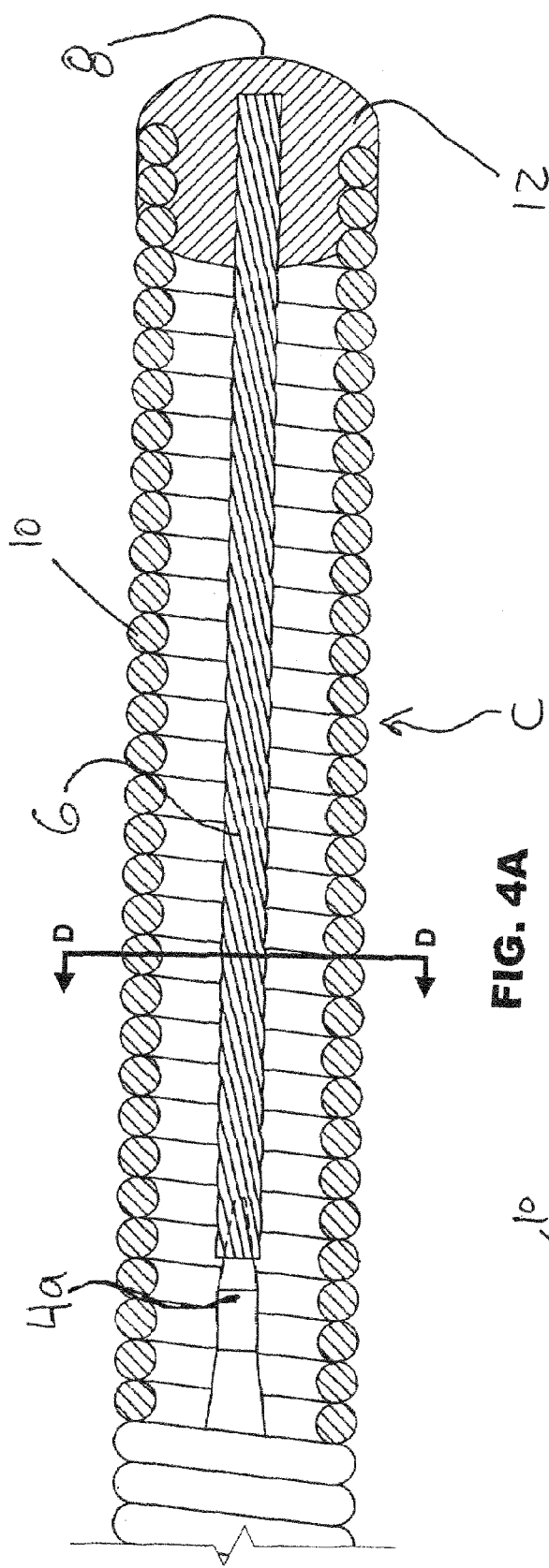
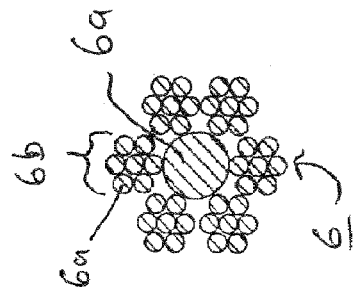
FIG. 4E
FIG. 4D
FIG. 4A
FIG. 4C
FIG. 4B

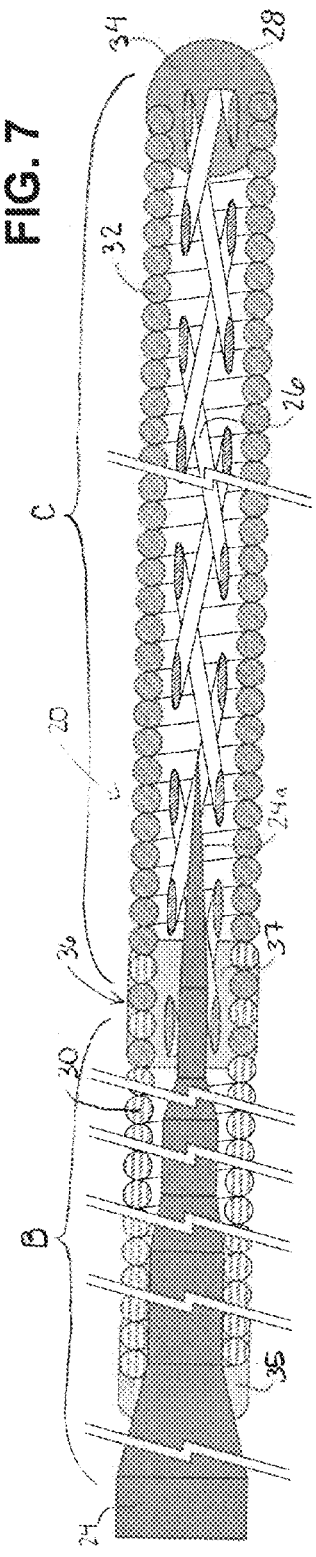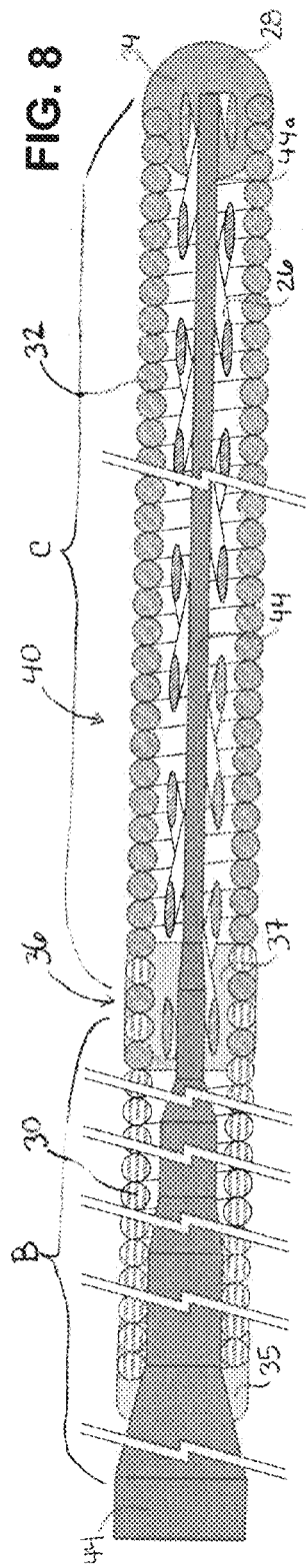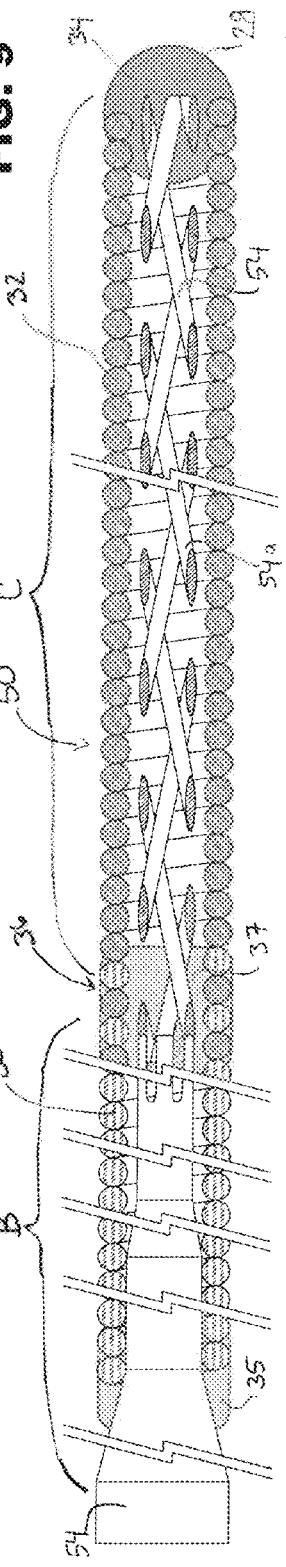

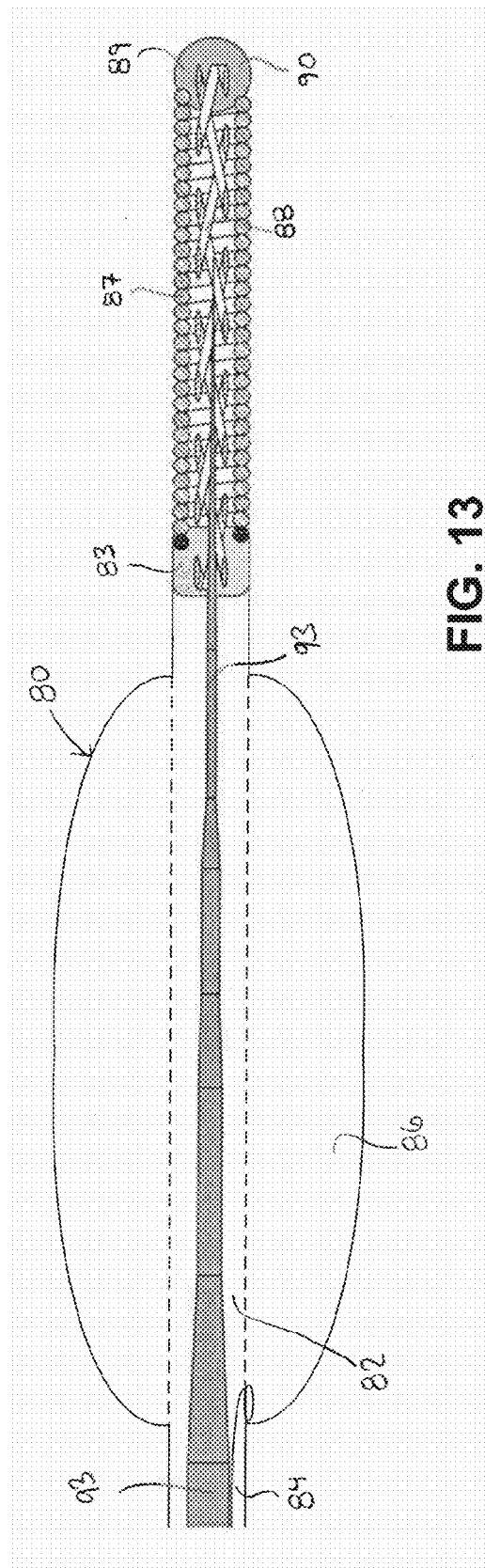
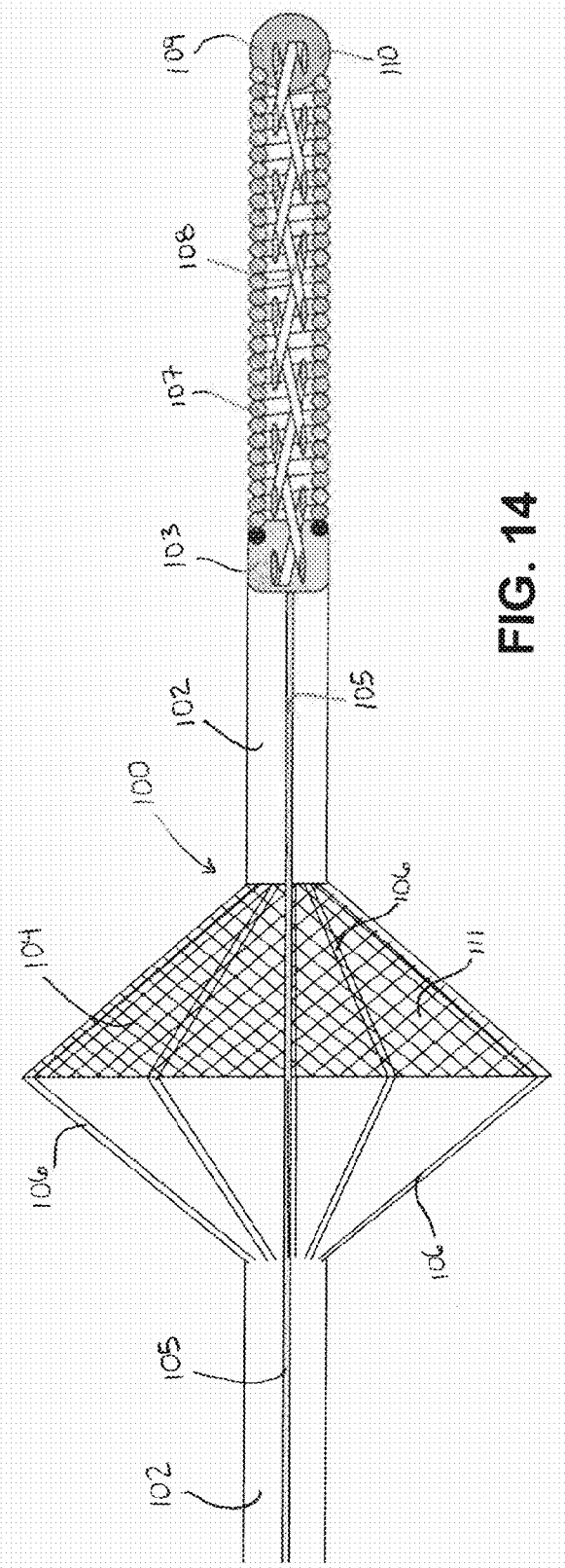

STEERABLE GUIDE WIRE WITH TORSIONALLY STABLE TIP

RELATED APPLICATIONS

This is a continuation of U.S. application Ser. No. 11/652,234, filed Jan. 10, 2007, now abandoned which is a continuation-in-part of U.S. application Ser. No. 11/176,485, filed Jul. 7, 2005, now U.S. Pat. No. 8,267,872 all of which are hereby expressly incorporated by reference in their entirety.

FIELD OF THE INVENTION

The field of the invention generally relates to guide wires. More particularly, the field of the invention relates to steerable guide wires used to access a site of interest inside a body lumen from a remote position located outside the body.

BACKGROUND OF THE INVENTION

Catheter based vascular interventions are becoming increasingly common in many of the vascular beds of the human body. For example, the treatment of obstructive plaque (e.g., stenosis) in coronary, peripheral, and cerebral arteries via angioplasty (with or without stents) has become a routine procedure. There remains a need, however, to improve the devices used in these procedures, to make them faster, easier, safer, and more viable, particularly in challenging anatomical situations.

The vast majority of catheter-based vascular interventions make use of a steerable guide wire to access the site of interest from a remote position outside the body. For example, in coronary interventions such as stent implantation, a steerable guide wire is advanced from the femoral artery access site into the various branches of coronary arteries and across the obstructive plaque. FIG. 5 illustrates the tip of a coronary guide wire accessing a coronary vessel with an obstructive plaque. After the guide wire is advanced past the stenosis, an interventional device such as a stent delivery balloon catheter (not shown) is advanced over the guide wire and through the stenosis. Thus, it is the guide wire that establishes the pathway for the interventional catheter that follows.

Steerability is an important performance characteristic for a steerable guide wire. Steerability generally refers to the ability to controllably rotate the distal tip of the guide wire to "point" the tip in the desired direction during the advancement procedure. Steerable guide wires typically have a "J" bend (for example, as seen in FIG. 5) imparted to the tip, either by the operator prior to the introduction into the body, or by the manufacturer. The ability to controllably orient this "J" bend allows the guide wire to be navigated into different branches of vessels and across the stenosis.

The ideal or optimum controllability of the tip of the guide wire is referred to as "1:1 torque response." This term refers to the ability of the tip to rotate exactly in step with rotation of the proximal end of the guide wire. For example, if the proximal end of the guide wire is rotated through 90 degrees, the tip will ideally rotate through 90 degrees—hence a 1:1 response.

Several factors influence the steerability qualities of a steerable guide wire. These include torsional stiffness of the guide wire components, dimensions, torsional modulus, guide wire straightness, guide wire resilience (ability to bend without plastically deforming), lubricity, and cross-sectional configuration. Steerability is also impacted by the tortuosity of the vascular anatomy.

Another important characteristic of a steerable guide wire is its tensile strength/integrity. This term generally refers to the guide wire's ability to withstand tensile forces applied to it without breaking. For example, the tips of guide wires occasionally get lodged in the stenosis or elsewhere in the vasculature, and when this happens, it is important to be able to dislodge the tip by pulling on the proximal end of the guide wire. The design of prior art steerable guide wires has thus involved a balance or trade-off between optimizing flexibility and steerability while at the same time maintaining tensile integrity.

FIGS. 1A-1D illustrates a typical construction of a prior art steerable guide wire, such as those commonly used in coronary interventions. As seen in FIG. 1A, the guide wire generally includes three portions, a proximal portion, a mid-portion, and a distal tip portion. There are two main components in steerable guide wires, a core wire that extends from a proximal end to a distal end, and a coil that extends over the mid-portion and tip portion of the guide wire. Lubricious coatings such as PTFE and/or hydrophilic or hydrophobic materials may also be present over some or all portions of the guide wire.

The core wire component of the guide wire is typically fabricated of high tensile strength stainless steel wire; however other materials are also used, such as NITINOL, MP35N, or ELGILOY. The guide wire is relatively stiff in the proximal portion and becomes increasingly more flexible towards the distal end. The proximal portion is typically of the original wire diameter (e.g., 0.014 inches for a coronary guide wire). The mid-portion is made more flexible by grinding down the diameter of the core wire to one or more smaller dimensions (e.g., 0.005 to 0.010 inches).

The distal tip portion of the guide wire is made even more flexible by further grinding of the core wire to a smaller dimension (e.g., 0.002 to 0.003 inches). While grinding the core wire to these smaller diameters does impart flexibility to the core wire, it is typically still not flexible enough for the tip portion to be atraumatic to the vasculature. Therefore the dimension of the core wire in the tip region is reduced even further by stamping or rolling the round wire into a flat ribbon configuration. The ribbon structure is illustrated in FIGS. 2A and 2B, as well as Section C-C in FIG. 1D. As seen in FIGS. 1D, 2A, and 2B, the ribbon is formed integrally with the core wire. In an alternative method of manufacture, however, it is also known to attach a separately formed piece of ribbon to a distal end of the mid portion of the core wire.

The high degree of flexibility achieved by the ribbon configuration could theoretically be accomplished by grinding the core wire to a round dimension that gives the equivalent stiffness of the ribbon. Unfortunately, however, the cross-sectional area of such a round wire would be substantially less than the cross-sectional area of the ribbon configuration. Therefore, the tensile integrity of the core wire would be significantly lowered. In a commonly used steerable coronary guide wire, the dimensions of the ribbon structure of the tip portion are approximately 0.001 by 0.003 inches. Such dimensions in a high tensile strength stainless steel core wire yield a tip portion with a high degree of flexibility and a tensile strength of approximately 0.9 lbs, which is close to the minimum acceptable tensile strength integrity for the tip portion of the guide wire.

While the prior art guide wire described above has a tip portion with good flexibility and acceptable tensile integrity, it does have compromised steerability as a result of the ribbon structure in the tip portion. The ribbon portion is typically about 2 cm in length. Any time the tip portion is positioned in a tortuous region of the vasculature (such as illustrated in FIG. 5), the ribbon will naturally bend only in the direction perpendicular to the ribbon's widest dimension (e.g., out of the plane of the page as shown in FIG. 2B). For a ribbon structure, there are thus only two stable bending directions 180 degrees apart from each other.

If, in this anatomical setting, the guide wire is rotated in an effort to steer the tip, the tip will resist rotating. Torque or energy will be stored in the ribbon in the form of a twist in the proximal region of the ribbon, as well as in the core wire extending proximally from the ribbon. Continued rotation of the proximal end of the guide wire will cause enough torque to build up such that the tip portion will suddenly rotate or "whip" to its next stable orientation. This orientation is 180 degrees from the previous orientation. Therefore, the ability to rotate the tip to orientations between 0 and 180 degrees is hampered. Similarly, if the guide wire is further rotated, the tip portion will again resist rotating until enough torque is built up and then the tip will suddenly rotate an additional 180 degrees.

There is thus a need for a steerable guide wire that exhibits controllable steering of the tip even in anatomically challenging vasculature. Such a steerable guide wire should have excellent steerability, tip flexibility, as well as tensile integrity. Moreover, there is a further need for a guide wire that is able to be rotated at the proximal end without any "whipping" of the distal tip.

SUMMARY OF THE INVENTION

The present invention provides for a steerable guide wire that dramatically improves steerability without compromising tensile integrity or flexibility.

In one aspect of the invention, a steerable guide wire includes a core wire having a proximal end and a distal end. A multi-filament bundle is affixed to the distal end of the core wire. An outer coil surrounds at least a portion of the core wire and the multi-filament bundle. A proximal end of the multi-filament bundle is secured to a distal end of the coil. By locating the multi-filament bundle in the distal tip portion of the guide wire, a guide wire is provided that is highly flexible, has a high degree of tensile integrity, and is highly steerable, even in tortuous vasculature.

In another aspect of the invention, a guide wire includes a proximal portion including a core wire and a distal portion that includes a multi-filament bundle coupled to the distal end of the core wire.

In yet another aspect of the invention, a guide wire includes a core wire having a proximal end and a distal end and a mufti-filament bundle disposed at the distal end of the core wire, the multi-filament bundle including a plurality of filaments that are twisted in a common direction. A coil surrounds at least a portion of the core wire and the multi-filament bundle.

In one aspect of the invention, the multi-filament bundle includes a central filament and a plurality of outer filaments. In an alternative aspect of the invention, the multi-filament bundle includes a central filament surrounded by a plurality of filament bundles. Each bundle includes a plurality of individual filaments.

In one aspect of the invention, the multi-filament bundle may be made of a central filament formed from a first material and a plurality of outer filaments formed from a second material. For example, the central filament may be formed from a radiopaque material.

In another aspect of this invention, a guide wire includes a core wire having a proximal end and a distal end. The guide wire also includes a braided filament disposed at the distal end of the core wire. A coil surrounds at least a portion of the core wire and the braided filament. In one embodiment, the core wire may extend through the braided filament to the distal end of the braided filament. In another embodiment, the core wire extends through only a portion of the braided filament. In yet another embodiment, the braided filament is unitary with the core wire.

In another aspect of this invention, a guide wire includes a core wire having a proximal end and a distal region, the distal region having a segment that comprises a slotted segment with repeating alternating first and second regions. In the slotted segment, the first region has a first cross-sectional width that is smaller than a second cross-sectional width of the second region. A coil surrounds at least a portion of the core wire.

In another aspect of this invention, a guide wire includes a core wire having a proximal end and a distal end. The guide wire also includes an elongate tubular member having a proximal end, a distal end, and a lumen therebetween, wherein at least a portion of the core wire is disposed within the lumen of the elongate tubular member. A coil surrounds at least a portion of the core wire and the elongate tubular member.

In another aspect of this invention, methods of use are provided for the above-described guide wires wherein the guide wires are advanced into a vessel of interest.

In another aspect of this invention, a balloon catheter includes an elongate tubular member having a proximal end, a distal region, a balloon disposed on the distal region, and an inflation lumen communicating with the balloon and extending proximally from the balloon. The balloon catheter also includes a braided filament extending distally from the distal region of the elongate tubular member and a coil surrounding at least a portion of the braided filament. The balloon may be a dilatation balloon or an occlusion balloon.

In another aspect of this invention, a method for using a dilatation balloon catheter to treat a vessel having a lesion is described. A balloon catheter as described above is provided, wherein the balloon catheter has a dilatation balloon disposed on the distal region. The balloon catheter is then advanced into the vessel and positioned such that the dilatation balloon is located at the lesion. The dilatation balloon is then expanded to dilate the lesion. Optionally, a catheter having a stent may then be advanced over the elongate tubular member and the stent may be expanded at the site of the lesion.

In another aspect of this invention, a method for using an occlusion balloon catheter to treat a vessel having a lesion is described. A balloon catheter as described above is provided, wherein the balloon catheter has an occlusion balloon disposed on the distal region. The balloon catheter is then advanced into the vessel and positioned such that the occlusion balloon is located distal the lesion. The occlusion balloon is then expanded to occlude the vessel. A catheter having a dilatation balloon may then be advanced over the elongate tubular member and the dilatation balloon may then be expanded to dilate the lesion. Additionally or alternatively, a catheter having a stent may be advanced over the elongate tubular member and the stent may be expanded at the site of the lesion.

It is an object of the invention to provide a guide wires and catheters that are highly flexible, have a high degree of tensile integrity, and are highly steerable, even in tortuous vasculature. Additional objects of invention are discussed below with reference to the drawings and the description of the preferred embodiments.

BRIEF DESCRIPTION OF THE DRAWINGS

FIG. 1A is a side view of a guide wire according to the prior art. FIG. 1A further includes partial cross-sectional views illustrating the core wire portion under the outer coil.

FIG. 1B is a cross-sectional view of the proximal shaft portion of the guide wire taken along the line A-A of FIG. 1A.

FIG. 1C is a cross-sectional view of the mid-shaft portion of the guide wire taken along the line B-B of FIG. 1A.

FIG. 1D is a cross-sectional view of the distal tip portion of the guide wire taken along the line C-C of FIG. 1A.

FIG. 2B illustrates the width of the ribbon structure according to the prior art.

FIG. 4A illustrates a magnified view of a cross-section of the distal tip portion of a guide wire according to one aspect of the invention.

FIG. 4B illustrates a cross-sectional view of the distal tip portion of the guide wire taken along the line D-D in FIG. 4A according to one embodiment of the invention.

FIG. 4C illustrates a cross-sectional view of the distal tip portion of the guide wire taken along the line D-D in FIG. 4A according to another embodiment of the invention.

FIG. 4D illustrates a cross-sectional view of the distal tip portion of the guide wire taken along the line D-D in FIG. 4A according to another embodiment of the invention.

FIG. 4E illustrates a cross-sectional view of the distal tip portion of the guide wire taken along the line D-D in FIG. 4A according to another embodiment of the invention.

FIG. 7 illustrates a magnified view of a cross-section of the distal tip portion of a guide wire having a braided filament according to one aspect of the invention.

FIG. 8 illustrates a magnified view of a cross-section of the distal tip portion of a guide wire having a braided filament according to another aspect of the invention.

FIG. 9 illustrates a magnified view of a cross-section of the distal tip portion of a guide wire having a braided region according to another aspect of the invention.

FIG. 13 illustrates a balloon catheter with a distal tip having a braided portion.

FIG. 14 illustrates a filter wire having a distal tip having a braided portion.

DETAILED DESCRIPTION OF THE PREFERRED EMBODIMENTS

Figure 2A:
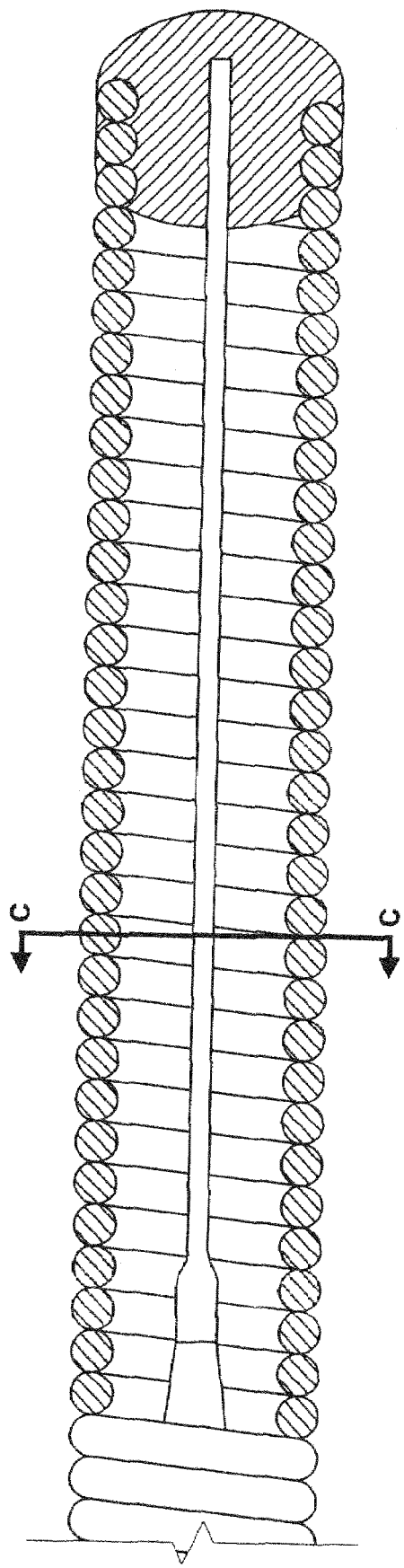
FIG. 2A is a magnified side view of the dashed region of FIG. 1A.
Figure 2B:
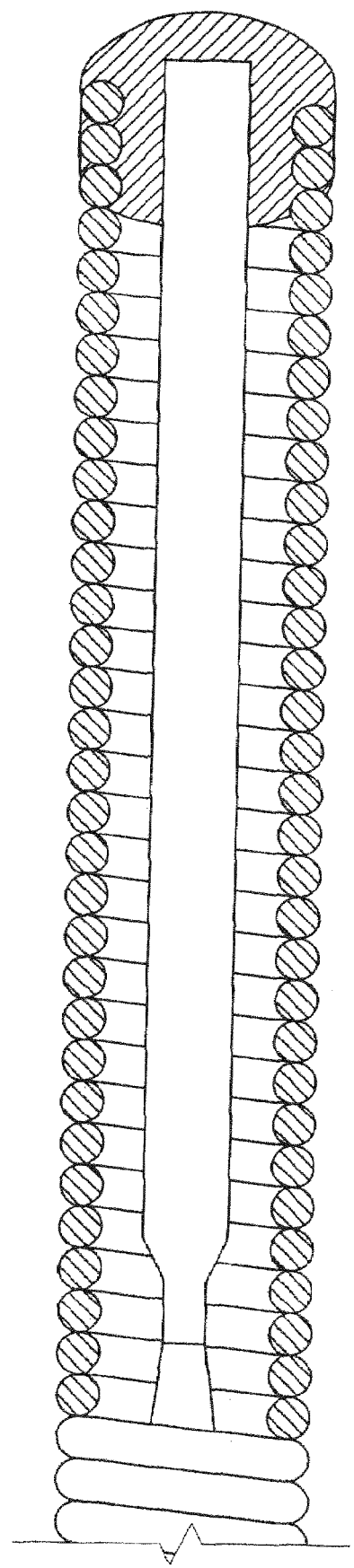
FIG. 2B is a magnified top view of the dashed region of FIG. 1A. The top view is generally perpendicular to the view shown in FIG. 2A.
Figure 3:
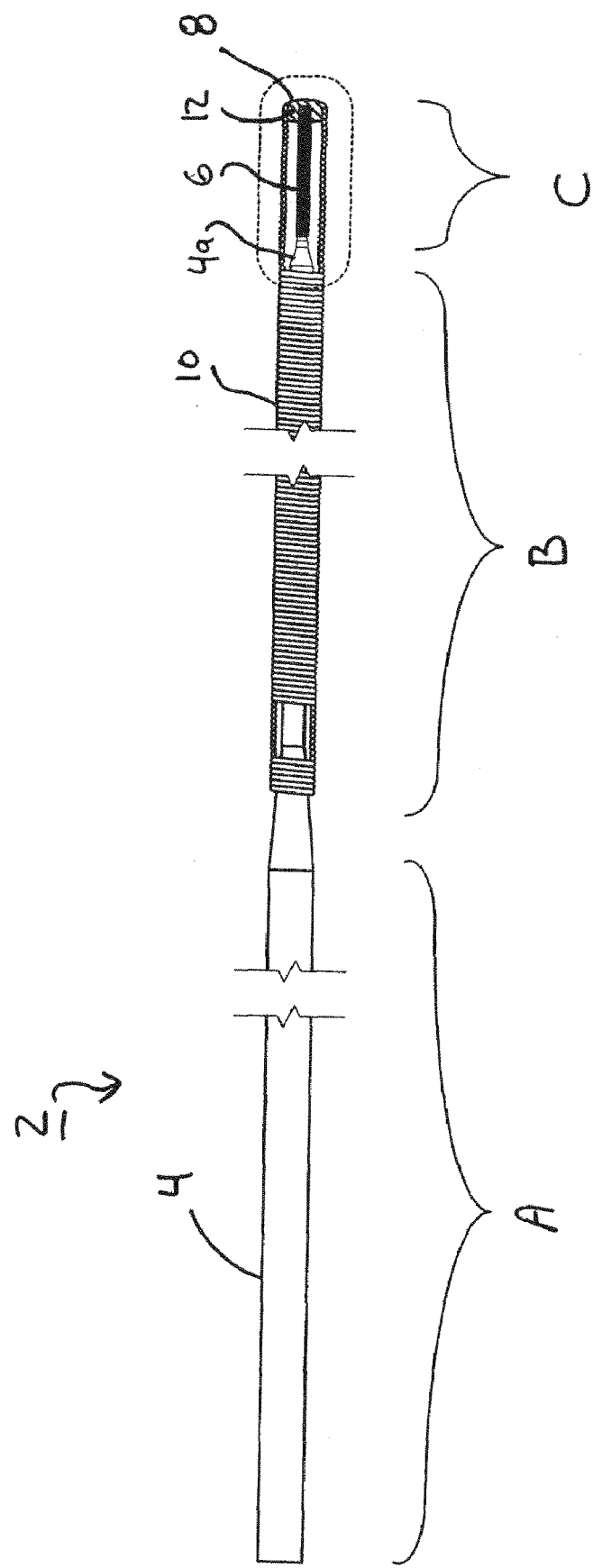
FIG. 3 illustrates side a view of a guide wire according to one aspect of the invention.

FIG. 3 illustrates a guide wire 2 according to one preferred aspect of the invention. The guide wire 2 generally includes a proximal portion A, a mid portion B, and a distal tip portion C. The guide wire 2 includes a solid core wire 4 that traverses the proximal and mid portions A, B and terminates in or near the distal tip portion C. As seen in FIG. 3, the diameter of the core wire 4 is reduced in the mid portion B of guide wire 2 to increase its flexibility. The distal end 4a of the core wire 4 is coupled to a multi-filament bundle 6. The multi-filament bundle 6 projects distally from the distal end 4a of the core wire 4 and terminates in a distal tip portion 8. The guide wire 2 further includes a coil 10 that is wrapped or wound around a portion of the exterior of the core wire 4 and multi-filament bundle 6. As seen in FIG. 3, the coil 10 begins in the mid portion B of the guide wire 2 and terminates at the distal tip 8. The distal tip 8 may include an end cap 12 such as a weld, braze, solder, adhesive, or the like to secure the distal most end of the multi-filament bundle 6.

The proximal and mid portions A, B of the guide wire 2 may be formed of any material suitable for guide wires including, but not limited to, 304 stainless steel, 316 stainless steel, NITINOL, MP35N, or ELGILOY. Fabrication of the proximal and mid portions A, B of the guide wire 2 may make use of methods and techniques such as center less grinding and/or chemical etching. The outer coil 10 may be formed of stainless steel or other suitable materials. In one aspect of the invention, the entire outer coil 10 or one or more sections thereof can incorporate radiopaque materials such as platinum/iridium, gold, or the like. Alternatively, in place of the outer coil 10, a polymer jacket, preferably loaded with radiopaque material such as barium sulfate or bismuth subcarbonate may be secured over all or portions of the core wire 4 and multi-filament bundle 6. Moreover, the guide wire 2 may include one or more lubricious coatings (not shown) that are applied to the guide wire 2 or portions thereof.

Still referring to FIG. 3, the core wire 4 terminates at or near the distal end of the mid portion B of the guide wire 2. In one preferred aspect of the invention, a multi-filament bundle 6 is attached or otherwise mechanically connected to the distal end of the core wire 4. The multi-filament bundle 6 extends to the distal tip portion 8 of the guide wire 2.

The multi-filament bundle 6 includes a plurality of individual filaments 6a that are arranged in a bundle, for example, as shown in FIG. 4A. In one aspect of the invention, the multi-filament bundle 6 may be formed of two or more individual wire filaments of high tensile strength material such as 304 stainless steel or 316 stainless steel or other suitable materials. In a preferred embodiment, the multi-filament bundle 6 may include stranded wire cable formed of seven wire filaments 6a, as depicted in FIG. 4B.

Alternatively, the multi-filament bundle 6 may be formed from three filaments 6a (e.g., wire filaments) as is depicted in FIG. 4C. A stranded wire cable comprising three or seven wire filaments 6a of the same diameter may be preferred as it is generally more structurally stable than stranded wire bundles of other numbers of wire filaments. However, the present guide wire 2 contemplates using a multi-filament bundle 6 of any number of filaments 6a greater than two. In addition, the multi-filament bundle 6 may be formed from a multi-filament inner core surrounded by a plurality of outer filaments.

In one aspect of the invention, the multi-filament bundle 6 includes a seven filament 6a stranded wire cable of high tensile strength stainless steel. The length of the multi-filament bundle 6 is preferably between 1 and 4 cm and most preferably about 2 cm, although other lengths are also contemplated by the scope of the present invention. The filaments 6a are preferably about 0.0005 inch to 0.0015 inch diameter and most preferably about 0.0008 to 0.0010 inch diameter.

For example, FIGS. 4A and 4B illustrate multi-filament bundle 6 in the form of a stranded wire bundle that is arranged with a central filament 6a surrounded by six outer filaments 6a all twisted in a common direction.

In an alternative embodiment, the multi-filament bundle 6 is formed from three filaments 6a as is depicted in FIG. 4C. In this embodiment, to achieve a tip portion of comparable flexibility to a guide wire 2 of the above embodiment (FIGS. 4A and 4B), the wire filaments 6a are preferably somewhat larger in diameter.

FIG. 4D illustrates a further embodiment wherein the central filament 6a is of a different dimension (i.e., diameter) than the outer filaments 6a'. For example, there may be a single central filament 6a and at least 7 outer filaments 6a'. FIG. 4E depicts a further alternative embodiment wherein the multi-filament bundle 6 includes one or more filament bundles 6b. As seen in FIG. 4E, a central filament 6a is surrounded by six filament bundles 6b. Each filament bundle 6b is formed from a plurality of filaments 6a.

Figure 5:
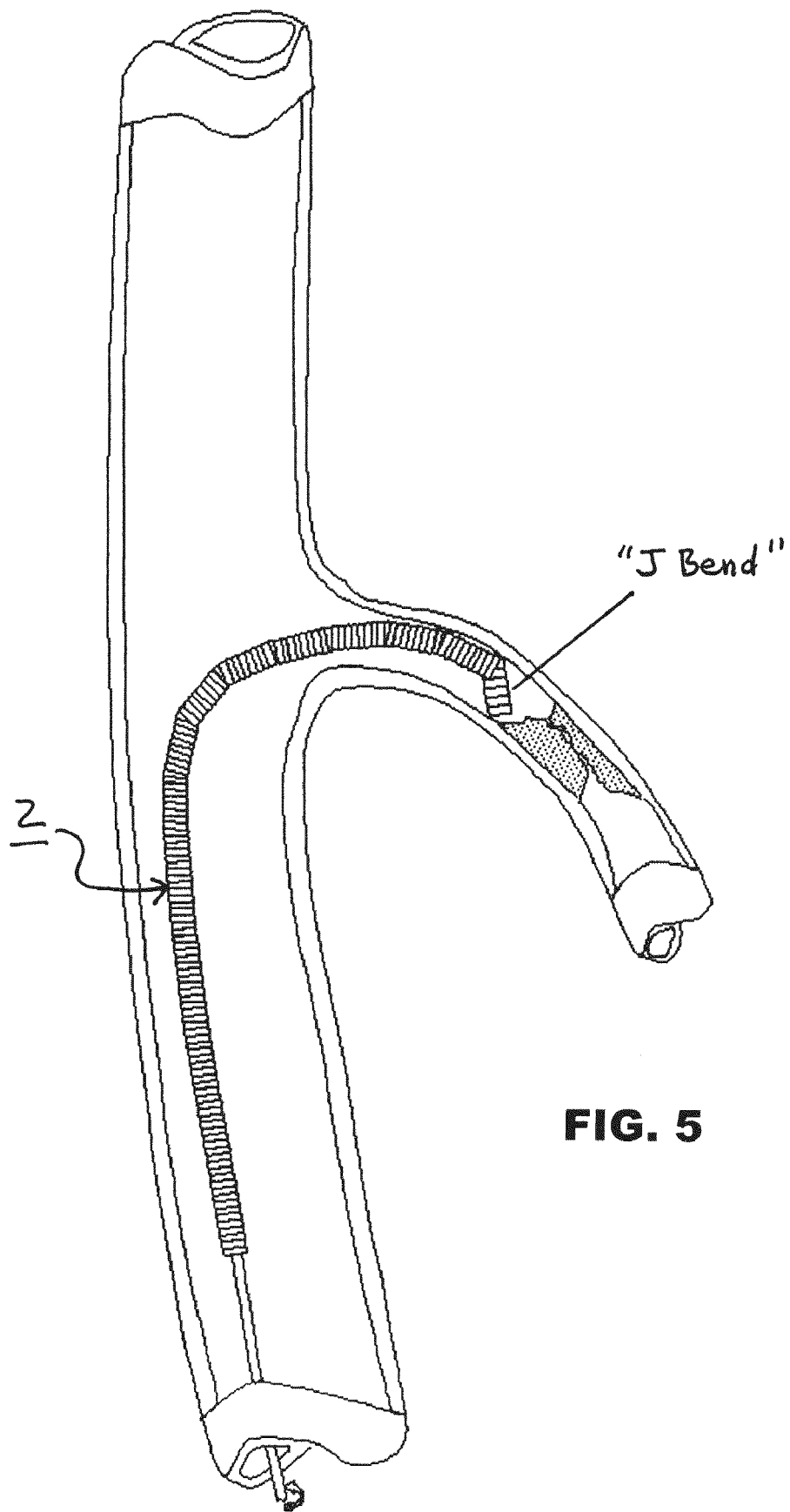
FIG. 5 illustrates a guide wire according to the present invention being advanced in a side branch of a vessel.

Each of the multi-filament bundle 6 arrangements depicted above can be tailored to have particular characteristics regarding flexibility, tensile strength, torsional stiffness, and tip formability (e.g., the ability to form a "J" bend such as that shown in FIG. 5). For instance, the arrangements depicted may incorporate one or more filaments 6a that are formed from different materials or have different properties than the other filament(s). By way of illustration and not limitation, in the arrangements depicted in FIGS. 4B and 4D, the central filament 6a may be fabricated of a radiopaque material such as platinum, while the outer filaments may be constructed of high tensile strength stainless steel. In yet another illustrative example, the central filament 6a could be fabricated of a more ductile material such as annealed or low tensile strength stainless steel and the outer filaments 6a' of high tensile strength stainless steel. This particular configuration would allow for the tip portion C to be highly formable yet retain high tensile strength due to the high tensile strength of the outer filaments 6a'.

In a further embodiment, the configuration depicted in FIGS. 4D and 4E may utilize high strength polymeric materials for one or more of the filaments 6a or filament bundles 6b. For example, in FIG. 4E, the central filament 6a could be formed of stainless steel and the outer filament bundles could be formed of a high strength polymer such as polyester, nylon, PTFE, or UHMWPE (Ultra High Molecular Weight Poly Ethylene) such as SPECTRA. The polymer bundles 6b could be twisted around the central filament 6a or, alternatively, they could be arranged in a braided configuration around central filament 6a.

Figure 6:
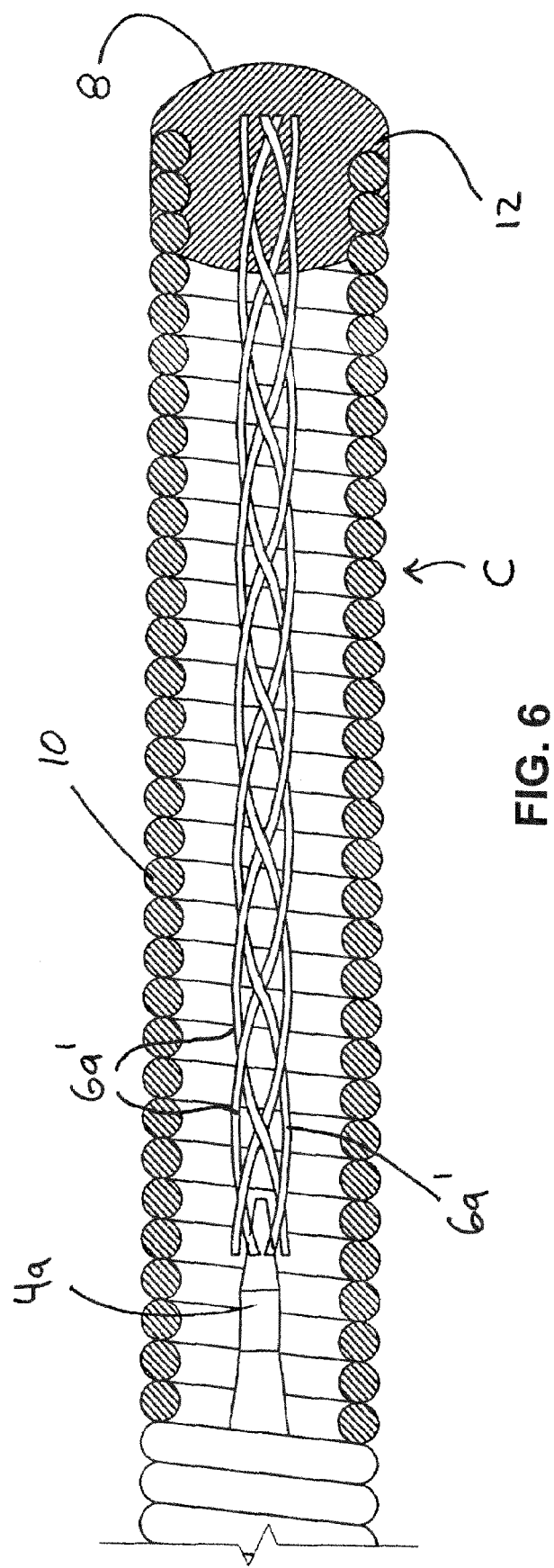
FIG. 6 illustrates a magnified view of a cross-section of the distal tip portion of a guide wire according to another aspect of the invention.

It is further contemplated that the arrangements depicted in FIGS. 4B and 4D could have the outer filaments 6a' arranged as a braid (not shown). Alternatively, one or more of the outer filaments 6a' could be wound in a direction opposite that of the other outer filaments 6a' (e.g., counter-wound filaments). It is also contemplated that in the arrangements of FIGS. 4B and 4D that if the outer filaments 6a are in a braided configuration, there may be no central filament 6a as is shown in FIG. 6.

The attachment of multi-filament bundle 6 to the distal end 4a of the core wire 4 can be accomplished by any suitable means such as soldering, brazing, welding, crimping band, shape recovery band, or adhesive bonding. The distal end of the multi-filament bundle 6 can be attached to the distal end of the outer coil 10 by suitable means including soldering, brazing, welding, or adhesive bonding.

FIG. 7 illustrates a guide wire 20 according to another preferred aspect of the invention. The guide wire 20 generally includes a proximal portion A (not shown), a mid portion B, and a distal tip portion C. The guide wire 20 includes a solid core wire 24 that traverses the proximal and mid portions A, B and terminates in or near the distal tip portion C. As seen in FIG. 7, the diameter of the core wire 24 is reduced in the mid portion B of guide wire 20 to increase its flexibility. The distal end 24a of the core wire 24 is coupled to a braided filament 26. The braided filament 26 projects distally from the distal end 24a of the core wire 24 and terminates in a distal tip 28. The distal end 24a of the core wire 24 may extend into approximately ¼ of the total length of the braided filament, alternatively into approximately ⅓ of the total length of the braided filament, alternatively into approximately ½ of the total length of the braided filament, approximately ¾ of the total length of the braided filament. The braided filament 26 may be about 2 cm in length, alternatively about 3 cm in length, alternatively about 4 cm in length, alternatively about 5 cm in length, alternatively about 6 cm in length, alternatively about 7 cm in length, alternatively about 8 cm in length. The guide wire 20 further includes first and second coils 30, 32 that surround a portion of the exterior of the core wire 24 and braided filament 26. As seen in FIG. 7, the first coil 30 begins in the proximal end of portion B of the guide wire 20 and terminates at around the proximal end of distal tip portion C. Second coil 32 begins at or around the proximal end of distal tip portion C and terminates at the distal tip 28. The material of the first coil is preferably stainless steel, and the material of the second coil is preferably a platinum alloy to provide radiopacity. The distal tip 28 may include an end cap 34 such as a weld, braze, solder, adhesive, or the like to secure the distal most end of the braided filament 26.

FIG. 8 illustrates a guide wire 40 according to another preferred aspect of the invention. The guide wire 40 generally includes a proximal portion A (not shown), a mid portion B, and a distal tip portion C. The guide wire 40 includes a solid core wire 44 that traverses the proximal and mid portions A, B and terminates at the distal end of the guide wire 40. As seen in FIG. 8, the diameter of the core wire 44 is reduced in the mid portion B of guide wire 40 to increase its flexibility. The core wire 44 in the distal tip portion is surrounded by a braided filament 26. Both the braided filament 26 and the core wire 44 terminate at the distal tip 28. The braided filament 26 may be about 2 cm in length, alternatively about 3 cm in length, alternatively about 4 cm in length, alternatively about 5 cm in length, alternatively about 6 cm in length, alternatively about 7 cm in length, alternatively about 8 cm in length. The guide wire 20 further includes first and second coils 30, 32 that are wrapped or wound around a portion of the exterior of the core wire 24 and braided filament 26. As seen in FIG. 8, the first coil 30 begins in the proximal end of portion B of the guide wire 20 and terminates at around the proximal end of distal tip portion C. Second coil 32 begins at or around the proximal end of distal tip portion C and terminates at the distal tip 28. The distal tip 28 may include an end cap 34 such as a weld, braze, solder, adhesive, or the like to secure the distal most ends of the braided filament 26 and the core wire 44.

FIG. 9 illustrates a guide wire 50 according to another preferred aspect of the invention. The guide wire 50 generally includes a proximal portion A (not shown), a mid portion B, and a distal tip portion C. The guide wire 50 includes a core wire 54 that traverses the proximal, mid portions, and distal tip portions A, B, and C and terminates at the distal end of the guide wire 50. As seen in FIG. 9, the diameter of the core wire 54 is reduced in the mid portion B of guide wire 40 to increase its flexibility. Core wire 54 has a unibody construction. In the distal tip portion C, a distal region of the core wire 54a has been cut into multiple strands (2, 3, 4, 5, or 6 strands) and the multiple strands have been braided or otherwise twisted together. Where there are four strands braided together, the distal region of the core wire 54a could be made by cutting a portion of the core wire in half to form two strands, turning the guide wire 90 degrees, and cutting the core wire in half again to form four total strands. The four strands could then be braided together or otherwise twisted together to form the distal end braided portion of the core wire. The braided region 54a of the core wire may be about 2 cm in length, alternatively about 3 cm in length, alternatively about 4 cm in length, alternatively about 5 cm in length, alternatively about 6 cm in length, alternatively about 7 cm in length, alternatively about 8 cm in length. The braided core wire 54 terminates at the distal tip 28. The guide wire 50 further includes first and second coils 30, 32 that are wrapped or wound around a portion of the exterior of the core wire 54. As seen in FIG. 9, the first coil 30 begins in the proximal end of portion B of the guide wire 50 and terminates at around the proximal end of distal tip portion C. Second coil 32 begins at or around the proximal end of distal tip portion C and terminates at the distal tip 28. The distal tip 28 may include an end cap 34 such as a weld, braze, solder, adhesive, or the like to secure the distal most end of the braided core wire 54.

Figure 10A:
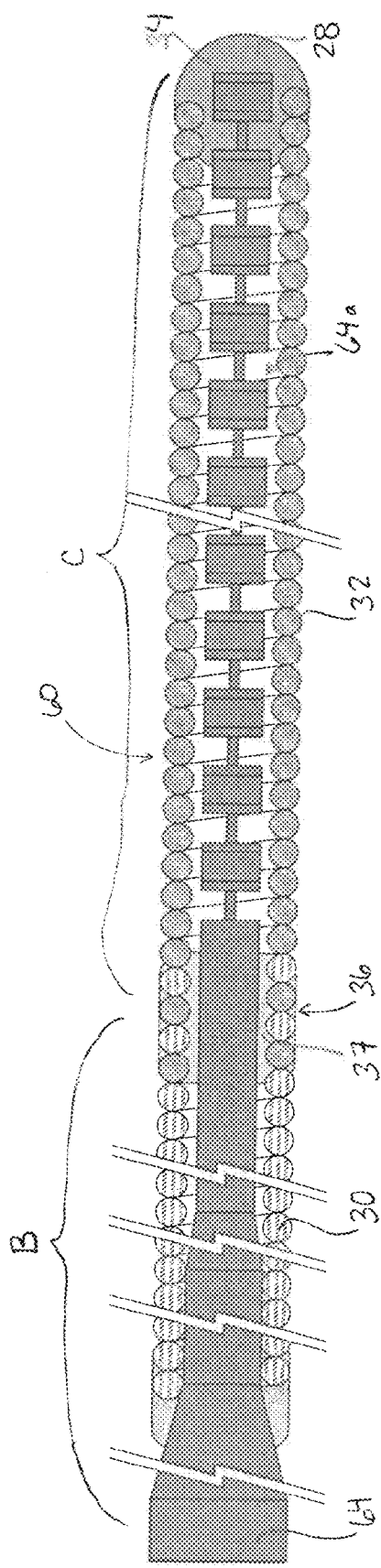
FIG. 10A illustrates a magnified view of a cross-section of the distal tip portion of a guide wire having a slotted region according to another aspect of the invention.
Figure 10B:
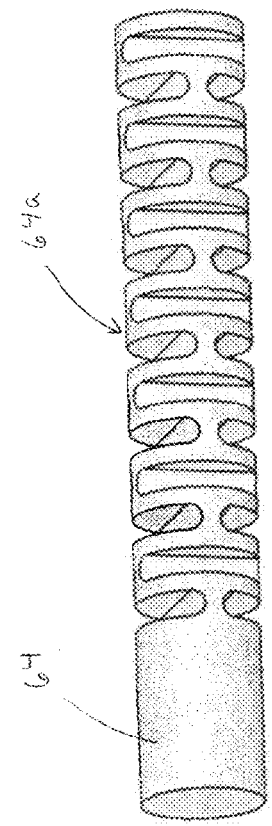
FIG. 10B illustrates an alternative view of the guide wire of FIG. 10A having a slotted region.

FIGS. 10A and B illustrate a guide wire 60 according to another preferred aspect of the invention. The guide wire 60 generally includes a proximal portion A (not shown), a mid portion B, and a distal tip portion C. The guide wire 60 includes a core wire 64 that traverses the proximal and mid portions A, B and terminates at the distal end of the guide wire 60. The core wire has a unibody construction and has a solid proximal portion and a slotted distal portion 64a. As seen in FIG. 10A, the diameter of the core wire 64 is reduced in the mid portion B of guide wire 40 to increase its flexibility. In the distal tip portion C, multiple slots have been cut into a distal region of the core wire 64a. The slotted segment 64a includes repeating alternating first and second regions, wherein the first region has a first cross-sectional width and the second region has a second cross-sectional width. In this slotted region, the first cross-sectional width is smaller than the second cross-sectional width. These alternating first and second regions can be repeated at least three times, alternatively at least 5 times, alternatively at least 7 times. The slotted core wire 64 terminates at the distal tip 28. The slotted region 64a of the core wire may be about 2 cm in length, alternatively about 3 cm in length, alternatively about 4 cm in length, alternatively about 5 cm in length, alternatively about 6 cm in length, alternatively about 7 cm in length, alternatively about 8 cm in length. The slotted segment could be made by laser cutting, electro-chemical etching, stamping, or electrical discharge machining. The guide wire 60 further includes first and second coils 30, 32 that are wrapped or wound around a portion of the exterior of the core wire 54. As seen in FIG. 10A, the first coil 30 begins in the proximal end of portion B of the guide wire 60 and terminates at around the proximal end of distal tip portion C. Second coil 32 begins at or around the proximal end of distal tip portion C and terminates at the distal tip 28. The distal tip 28 may include an end cap 34 such as a weld, braze, solder, adhesive, or the like to secure the distal most end of the slotted core wire 44a.

Figure 11:
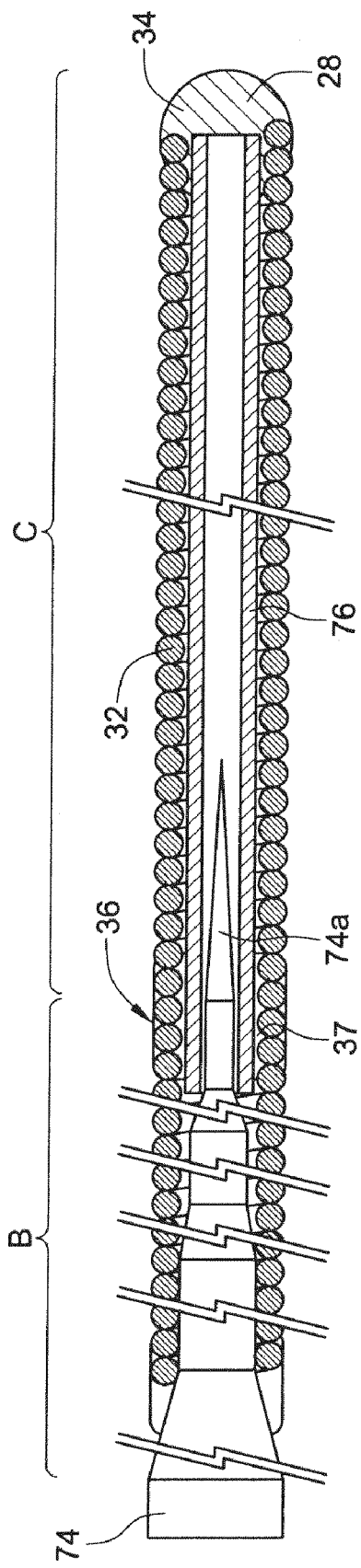
FIG. 11 illustrates a magnified view of a cross-section of the distal tip portion of a guide wire having an elongate tubular member extending from a core wire according to another aspect of the invention.

FIG. 11 illustrates a guide wire 70 according to another preferred aspect of the invention. The guide wire 70 generally includes a proximal portion A (not shown), a mid portion B, and a distal tip portion C. The guide wire 70 includes a solid core wire 74 that traverses the proximal and mid portions A, B and terminates in or near the distal tip portion C. As seen in FIG. 11, the diameter of the core wire 74 is reduced in the mid portion B of guide wire 20 and tapers to a pointed or wedge-shaped distal tip to increase its flexibility. The distal end 74a of the core wire 74 is coupled to the elongate tubular member 76. In one embodiment, the distal end 74a of the core wire 74 may be disposed within a lumen of the elongate tubular member 76. A solder joint may also couple the distal end 74a of the core wire 74 to the elongate tubular member 76. The elongate tubular member 76 projects distally from the distal end 74a of the core wire 74 and terminates in a distal tip 28. The elongate tubular member 76 could be made of a biocompatible metal such as nitinol or a polymer. The elongate tubular member 76 may also include slots to increase the flexibility of the tubular member. The slots may be made using laser cutting, die cutting, etching, or electrical discharge machining. The goal of the design is to enable the doctor to be able to torque the guide wire without whipping the tip when navigating tortuous anatomy. A 1:1 steering response to torque response is desired. The guide wire 70 further includes first and second coils 30, 32 that are wrapped or wound around a portion of the exterior of the core wire 74 and elongate tubular member 76. As seen in FIG. 11, the first coil 30 begins in the proximal end of portion B of the guide wire 70 and terminates at around the proximal end of distal tip portion C. Second coil 32 begins at or around the proximal end of distal tip portion C and terminates at the distal tip 28. The distal tip 28 may include an end cap 34 such as a weld, braze, solder, adhesive, or the like to secure the distal most end of the elongate tubular member 76.

With reference to the above embodiments, the proximal and mid portions A, B of the guide wire may be formed of any material suitable for guide wires including, but not limited to, 304 stainless steel, 316 stainless steel, NITINOL, MP35N, or ELGILOY. Fabrication of the proximal and mid portions A, B of the guide wire may make use of methods and techniques such as center less grinding and/or chemical etching.

In the above embodiments, the first and second coils 30, 32 are wrapped around a portion of the mid-portion and distal tip portion of the guide wire. The first coil 30, which is wrapped around at least a portion of mid-portion B of the guide wire, may be made out of a biocompatible material such as stainless steel. The first coil may be approximately 10-22 cm long, alternatively approximately 12-20 cm long, alternatively approximately 14-20 cm long. The second coil 32, which is wrapped around at least a portion of distal tip portion C of the guide wire, may be made out of a biocompatible material such as platinum or a platinum-containing alloy such as Platinum-Iridium or Platinum-Tungsten, or a combination thereof. The second coil 32 may be approximately 2 cm long, alternatively approximately 3 cm long, alternatively approximately 4 cm long, alternatively approximately 5 cm long, alternatively approximately 6 cm long. The proximal end of the first coil may be attached to the core wire through a solder joint 35. The distal end of the first coil and the proximal end of the second coil may be connected or otherwise coupled together. In one embodiment, the first and second coils may be joined in a threaded region 36, i.e., at least one turn of the distal end of the first coil may be threaded into at least one turn of the proximal end of the second coil. Additionally, the threaded region 36 may be coupled to the core wire through a solder joint 37. Alternatively, in another embodiment, the coils may not be threaded together but may be joined to each other and/or the core wire with one or more solder joints.

Figure 12A:
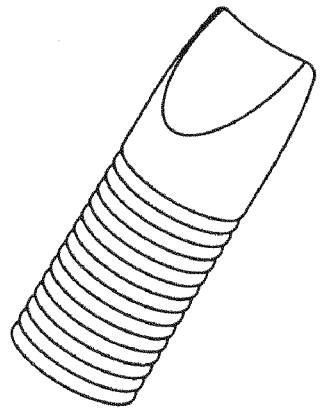
FIG. 12A illustrates a magnified view of a distal end of a guide wire having a tip weld with a tapering, rounded tip.
Figure 12B:
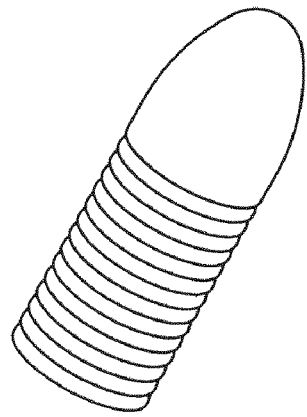
FIG. 12B illustrates a magnified view of a distal end of a guide wire having a tip weld with a pointed or wedge-shaped tip.

In the above embodiment, the distal end of guide wire ends in a tip weld 34. Depending on the embodiment, as seen in FIG. 7, the tip weld 34 may join the braided filament 26 and the second coil 32. Alternatively, as seen in FIG. 8, the tip weld may join the core wire, the braided filament 26, and the second coil 32. Alternatively, as seen in FIG. 9, the tip weld may join the braided portion 54a of the core wire and the second coil 32. Alternatively, as seen in FIG. 10A, the tip weld may join the slotted portion 64a of the core wire and the second coil 32. Alternatively, as seen in FIG. 11, the tip weld may join the elongate tubular member 76 and the second coil 32. The tip weld may have a rounded portion and/or have a distal portion that is substantially hemispherical in shape (see FIGS. 7-10A). Alternatively, the tip weld may have a tapered shape, as seen in FIG. 12A. The tip weld may also have a wedge shape, as seen in FIG. 12B.

The configurations described above that make use of braided or counter-wound filaments 6a or filament bundles 6b have enhanced torsional strength. However, these configurations also have increased total or "effective" diameters. Depending on the intended application of the invention, particular configurations may be preferred.

The multi-filament or braided filament bundle is rotationally stable, i.e., it does not have a preferred bending direction as does the prior art ribbon configuration. Therefore, if multi-filament or braided filament bundle is placed in a tortuous anatomy such as that depicted in FIG. 5, the guide wire will permit the distal tip of the guide wire to be oriented in any direction in a controllable fashion. The distal tip of the guide wire will advantageously have a 1:1 response or a substantially 1:1 torque response. Moreover, the guide wire eliminates the "whipping" motion that heretofore accompanied guide wires that utilized a ribbon structure at the distal tip.

The filament or braided filament bundle is more flexible than a solid structure of equivalent diameter, yet retains approximately the same tensile strength as a solid structure of the same equivalent diameter. This characteristic advantageously allows for a filament or braided filament bundle to have both high flexibility and high tensile strength. Unlike the prior art ribbon configuration, however, the filament or braided filament bundle is rotationally stable. Consequently, a guide wire making use of the multifilament bundle in the distal tip portion C can be highly flexible, have high tensile integrity, and be highly steerable, even in tortuous vasculature. In one preferred aspect of the invention, the distal tip portion of the guide wire has substantially uniform stiffness in all radial directions.

FIG. 13 illustrates a medical device according to another preferred aspect of the invention. Balloon catheter 80 includes an elongate tubular member 82 having a proximal end, a distal region and a lumen, balloon 86 located on the distal region, inflation lumen 84 communicating with the balloon and extending proximally from balloon 86, and core wire 93 disposed within the lumen. The distal region of balloon catheter 80 further includes braided filament 88 that extends distally from the distal region of elongate tubular member 82. Braided filament 88 may be coupled to elongate tubular member 82 and/or core wire 93 by solder joint 83. Braided filament 88 terminates at the distal tip 89. The braided filament 88 may be about 2 cm in length, alternatively about 3 cm in length, alternatively about 4 cm in length, alternatively about 5 cm in length, alternatively about 6 cm in length, alternatively about 7 cm in length, alternatively about 8 cm in length. Balloon catheter 80 further includes coil 87 that surrounds at least a portion of braided filament 88 and terminates at the distal tip 89. The distal tip 89 may include an end cap 90 such as a weld, braze, solder, adhesive, or the like to secure the distal most ends of the braided filament 88. Distal tip 89 may have a substantially hemispherical or round shape; alternatively, it could have a tapered or pointed shape. Balloon 86 may be either be an occlusion balloon or a dilatation balloon.

In use, the balloon catheter may be advanced into a vessel containing a lesion. Where the balloon is a dilatation balloon, the balloon may be located at the site of the lesion. The balloon may then be expanded to dilate the lesion. Where the balloon is an occlusion balloon, after the balloon is advanced into the vessel containing the lesion, the balloon may be located distal the lesion. A catheter having a dilatation balloon may then be advanced over the elongate tubular member and the dilatation balloon may then be expanded to dilate the lesion. Alternatively, the catheter may include a stent disposed about the dilatation balloon.

FIG. 14 illustrates a medical device according to another preferred aspect of the invention. Filter catheter 100 includes an elongate tubular member 102 having a proximal end, a distal region, expandable filter 104 located on the distal region, and actuation mechanism 105 operable to expand the filter. Expandable filter 104 includes a plurality of struts 106, at least a portion of which is covered by porous material 111, such as a mesh material. The distal region of filter catheter 100 further includes braided filament 108 that extends distally from the distal region of elongate tubular member 102. Braided filament 108 may be coupled to the distal end of elongate tubular member 102 through solder joint 103. Braided filament 108 terminates at the distal tip 109. The braided filament 108 may be about 2 cm in length, alternatively about 3 cm in length, alternatively about 4 cm in length, alternatively about 5 cm in length, alternatively about 6 cm in length, alternatively about 7 cm in length, alternatively about 8 cm in length. Filter catheter 100 further includes coil 107 that surrounds at least a portion of braided filament 108 and terminates at the distal tip 109. The distal tip 109 may include an end cap 110 such as a weld, braze, solder, adhesive, or the like to secure the distal most ends of the braided filament 108. Distal tip 109 may have a substantially hemispherical or round shape; alternatively it could have a tapered or pointed shape.

In use, the filter catheter may be advanced into a vessel containing a lesion such that the expandable filter is located distal the lesion. The actuation mechanism can then be operated to expand the expandable filter. Once the filter is expanded, a catheter having a dilatation balloon could be advanced over the elongate tubular member of the filter catheter and the dilatation balloon could be expanded at the site of the lesion. Additionally or alternatively, a catheter having a stent could be advanced over the elongate tubular member and the stent could be expanded at the site of the lesion.

While embodiments of the present invention have been shown and described, various modifications may be made without departing from the scope of the present invention. The invention, therefore, should not be limited, except to the following claims, and their equivalents.

What is claimed is:

1. A guide wire comprising:
   a core wire having a proximal end and a distal end;
   a braided filament disposed at the distal end of the core wire, wherein at least a portion of the braided filament surrounds the distal end of the core wire; and
   a coil surrounding at least a portion of the core wire and the braided filament;
   wherein the core wire, braided filament and coil are connected together at a distal tip of the guide wire.

2. The guide wire of claim 1, wherein the braided filament is joined to the core wire by a solder joint.

3. The guide wire of claim 1, wherein the braided filament is joined to the core wire and the coil by a solder joint.

4. The guide wire of claim 1, wherein the coil is joined to the core wire by a solder joint.

5. The guide wire of claim 1, wherein the coil is joined to the braided filament by a solder joint.

6. The guide wire of claim 1, wherein the core wire is tapered in a distal region.

7. The guide wire of claim 1, wherein the coil comprises at least one of platinum, a platinum alloy, or stainless steel.

8. The guide wire of claim 2, wherein the platinum alloy is platinum-iridium or platinum-tungsten.

9. The guide wire of claim 1, wherein the coil comprises a proximal coil segment and a distal coil segment.

10. The guide wire of claim 9, wherein the distal coil segment, the proximal coil segment, the braided filament, and the core wire are joined by a solder joint.

11. The guide wire of claim 9, wherein the distal coil segment is coupled to the proximal coil segment.

12. The guide wire of claim 11, wherein the distal coil segment is coupled to the proximal coil segment by threading a proximal end of the distal coil segment into a distal end of the proximal coil segment.

13. The guide wire of claim 1, further comprising a tip weld at a distal end of the guide wire.

14. The guide wire of claim 13, wherein the tip weld joins a distal end of the coil to a distal end of the braided filament.

15. The guide wire of claim 13, wherein the tip weld has a substantially hemispherical distal portion.

16. The guide wire of claim 13, wherein the tip weld has a rounded distal portion.

17. The guide wire of claim 13, wherein the tip weld has a pointed tip.

18. The guide wire of claim 13, wherein the tip weld has a wedge-shaped tip.

19. The guide wire of claim 13, wherein the tip weld has a tapered tip.

20. The guide wire of claim 1, wherein the core wire extends through a portion of the braided filament.

21. The guide wire of claim 1, wherein the core wire extends through the braided filament to a distal end of the braided filament.

22. The guide wire of claim 1, wherein the core wire extends through the braided filament to a tip weld at the distal end of the guide wire.

23. The guide wire of claim 1, wherein the braided filament is unitary with the core wire.

24. A guide wire comprising:
  a core wire having a proximal portion, a mid portion, a distal portion, and a distal end;
  a braided filament disposed at the distal end of the core wire, wherein at least a portion of the braided filament surrounds the distal end of the core wire;
  a first coil surrounding at least a portion of the mid portion of the core wire, and
  a second coil surrounding at least a portion of the distal portion of the core wire and the braided filament;
  wherein the core wire, braided filament and second coil are connected together at a distal tip of the guide wire.

25. The guide wire of claim 24, wherein a distal portion of the first coil is interwound with a proximal portion of the second coil.

26. The guide wire of claim 24, wherein the first coil is made from stainless steel.

27. The guide wire of claim 24, wherein the second coil is radiopaque.

28. The guide wire of claim 24, wherein the second coil is made from a platinum alloy.

* * * * *